(12) United States Patent
Orth et al.

(10) Patent No.: US 8,956,452 B2
(45) Date of Patent: Feb. 17, 2015

(54) METHOD FOR PRODUCING RHEOLOGICALLY EFFECTIVE UREA URETHANES IN ORGANIC SALTS

(75) Inventors: Ulrich Orth, Wesel (DE); Marc Eberhardt, Wesel (DE); Jurgen Omeis, Dorsten-Lembeck (DE); Christian Dams, Xanten (DE)

(73) Assignee: BYK-Chemie GmbH (DE)

( * ) Notice: Subject to any disclaimer, the term of this patent is extended or adjusted under 35 U.S.C. 154(b) by 813 days.

(21) Appl. No.: 13/130,349

(22) PCT Filed: Nov. 11, 2009

(86) PCT No.: PCT/EP2009/008043
§ 371 (c)(1),
(2), (4) Date: Jun. 28, 2011

(87) PCT Pub. No.: WO2010/063358
PCT Pub. Date: Jun. 10, 2010

(65) Prior Publication Data
US 2011/0265691 A1 Nov. 3, 2011

(30) Foreign Application Priority Data
Dec. 1, 2008 (DE) .......................... 10 2008 059 702

(51) Int. Cl.
| | | |
|---|---|---|
| C08K 5/00 | (2006.01) | |
| C08G 18/28 | (2006.01) | |
| C07C 273/18 | (2006.01) | |
| C07C 275/40 | (2006.01) | |
| C08G 18/10 | (2006.01) | |
| C08G 18/32 | (2006.01) | |
| C08G 18/80 | (2006.01) | |
| C09D 5/04 | (2006.01) | |

(52) U.S. Cl.
CPC .......... *C08G 18/2815* (2013.01); *C07C 273/18* (2013.01); *C07C 273/1827* (2013.01); *C07C 275/40* (2013.01); *C08G 18/10* (2013.01); *C08G 18/282* (2013.01); *C08G 18/2825* (2013.01); *C08G 18/283* (2013.01); *C08G 18/284* (2013.01); *C08G 18/3225* (2013.01); *C08G 18/8064* (2013.01); *C09D 5/04* (2013.01)
USPC ....................................................... 106/505

(58) Field of Classification Search
None
See application file for complete search history.

(56) References Cited

U.S. PATENT DOCUMENTS

| | | | |
|---|---|---|---|
| 4,314,924 | A | 2/1982 | Haubennestel et al. |
| 4,851,294 | A | 7/1989 | Buter et al. |
| 5,874,638 | A | 2/1999 | Chauvin et al. |
| 2002/0115882 | A1 | 8/2002 | Haubennestel et al. |
| 2007/0010688 | A1 | 1/2007 | Ke et al. |

FOREIGN PATENT DOCUMENTS

| | | |
|---|---|---|
| CA | 2352660 A1 | 2/2002 |
| EP | 0006252 A1 | 1/1980 |
| EP | 0198519 A1 | 10/1986 |
| EP | 0776880 A1 | 6/1997 |
| EP | 1182197 A1 | 2/2002 |
| EP | 1188779 A1 | 3/2002 |
| JP | 2002105042 A | 4/2002 |
| JP | 2006249166 A | 9/2006 |
| JP | 2006316041 A | 11/2006 |
| JP | 2008514694 A | 5/2008 |
| WO | WO-96/18459 A1 | 6/1996 |

OTHER PUBLICATIONS

Qian "Facile Synthesis of Ureas in Ionic Liquids" Chinese Chemical Letters, 15 (11), 2004, p. 1269-1272, abstract only.*
Qian "Facile Synthesis of Ureas in Ionic Liquids" Chinese Chemical Letters, 15 (11), 2004, p. 1269-1272—full document.*
"International Application No. PCT/EP2009/008043, International Search Report and Written Opinion issued May 20, 2010", (May 20, 2010), 14 pgs.
Chauvin, Y., et al., "A Novel Class of Versatile Solvents for Two-Phase Catalysis: Hydrogenation, Isomerization, and Hydroformylation of Alkenes Catalyzed by Rhodium Complexes in Liquid 1,3-Dialkylimidazolium Salts", Angew. Chem., Int. Ed. Engl., 34(23-24), (1995), 2698-2700.
Fuller, J., et al., "Structure of 1-ethyl-3-methylimidazolium hexafluorophosphate: model for room temperature molten salts", Journal of the Chemical Society, Chemical Communications, 3, (1994), 299-300.
Keim, W., et al., "New Method to Recycle Homogenous Catalysts from Monophasic Reaction Mixtures by Using an Ionic Liquid Exemplified for the Rh-Catalysed Hydroformylation of Methyl-3-pentenoate", Journal of Catalysis, 186(2), (1999), 481-484.
Suarez, Paulo A. Z., et al., "The use of new ionic liquids in two-phase catalytic hydrogenation reaction by rhodium complexes", Polyhedron, 15(7), (1996), 1217-1219.
Suarez, Paulo A.Z., et al., "Two-phase catalytic hydrogenation of olefins by Ru(II) and Co(II) complexes dissolved in 1-n-butyl-3-methylimidazolium tetrafluoroborate ionic liquid", Inorganica Chimica Acta, 255(1), (Feb. 1, 1997), 207-209.
Welton, T., "Room-Temperature Ionic Liquids. Solvents for Synthesis and Catalysis", Chemical Reviews, 99(8), (1999), 2071-2083.

(Continued)

*Primary Examiner* — Fereydoun G Sajjadi
*Assistant Examiner* — Amy C Bonaparte
(74) *Attorney, Agent, or Firm* — Schwegman Lundberg & Woessner, P.A.

(57) ABSTRACT

The invention relates to a method for producing a solution comprising urea urethanes and acting as a thixotropic agent, wherein at least two structurally different monohydroxy compounds are converted by an excess of toluoylene diisocyanate, forming monoisocyanate adducts having diamines in an ionic fluid, forming urea urethanes. The invention further relates to the use of the solution for thixotroping coating agents and solutions of urea urethanes in ionic fluids.

18 Claims, No Drawings

(56) References Cited

OTHER PUBLICATIONS

Wilkes, J. S, et al., "Air and water stable 1-ethyl-3-methylimidazolium based ionic liquids", Journal of the Chemical Society, Chemical Communications, 13, (1992), 965-967.

"International Application No. PCT/EP2009/008043, English Translation of International Preliminary Report on Patentability mailed Jun. 16, 2011", (Jun. 16, 2011), 7 pgs.

"International Application No. PCT/EP2009/008043, Written Opinion issued May 20, 2010", (English Translation), 5 pgs.

* cited by examiner

METHOD FOR PRODUCING RHEOLOGICALLY EFFECTIVE UREA URETHANES IN ORGANIC SALTS

PRIORITY CLAIM TO RELATED APPLICATIONS

This application is a national stage application under 35 U.S.C. §371 of PCT/EP2009/008043, filed Nov. 11, 2009, and published as WO 2010/063358 A1 on Jun. 10, 2010, which claims priority to German Application No. 10 2008 059 702.3, filed Dec. 1, 2008, which applications and publication are incorporated herein by reference and made a part hereof in their entirety, and the benefit of priority of each of which is claimed herein.

This invention relates to a method for producing a solution comprising urea urethanes which is efficacious as a thixotropic agent, wherein monohydroxy compounds are reacted with an excess of tolylene diisocyanate, the unconverted tolylene diisocyanate is removed from the reaction mixture and the resulting monoisocyanate adducts are further reacted with diamines in an ionic liquid to form urea urethanes. This invention further relates to the use of the solution for thixotroping coating materials.

The rheology of liquid coating systems is currently still mostly controlled using organically modified bentonites, silicas, hydrogenated castor oil and polyamide waxes. These substances are disadvantageous in that they are usually dry solids which have to be solvent and shear destructurized to an intermediate product which has to be incorporated in the liquid coating system under specific temperature control. If these temperatures are not maintained, crystallites occur in the final coating system and can lead to defects in the coating.

The general disadvantage of these rheological aids is that they lead to clouding and haze in clear transparent coatings. Moreover, handling dry pulverulent products which give rise to dusts during processing is undesirable.

Other rheology control solutions were presented in European patent application EP-A-0 198 519. There an isocyanate is reacted with an amine in the presence of coating resin solutions to form a urea which forms acicular crystals in very finely disperse form. These coating binders thus modified are offered as rheology-controlling and sag-preventing binders known as sag control agents. The disadvantage with these products is that they are always tied to the binders in which they were produced, and do not permit subsequent universal correction of final coating materials.

European patent EP-B-0 006 252 describes a process for preparing a thixotropic agent where some of the abovementioned disadvantages are dispelled by describing urea urethanes which are prepared in aprotic solvents in the presence of lithium salts by reaction of isocyanate adducts with polyamines. However, the products prepared in this way have two significant disadvantages. First, these thixotropic agents have an undefined structure due to their method of synthesis.

These products then exhibit a propensity toward precipitation phenomena and are very difficult to keep in solution. Secondly, a further disadvantage of the thixotropic agents produced by this process is that only monoisocyanate adducts of the same structure are reacted with the diamine. This in turn leads to limited compatibility in the coating systems used, which manifests in gel bodies or severe clouding, and further to inferior rheological efficacy.

Proceeding from the aforementioned prior art, EP-B-1 188 779 provided thixotropic agents which do have a defined structure, provide greater storage stability of the solution over several months, are notable for broader compatibility in binders and hence ensure more consistent use of the products. These thixotropic agents were prepared in an aprotic medium, more particularly N-methylpyrrolidone (NMP), in the presence of major quantities of lithium salts, more particularly lithium chloride.

However, there are disadvantages with both the use of N-methylpyrrolidone and with the use of lithium salts. N-Methylpyrrolidone and other solvents mentioned in European patent specification EP-B-1 188 779 are not generally recognized as safe by toxicologists, and therefore are no longer acceptable for further use in coating systems. The mandatory use of lithium salts and other metal salts in turn has the disadvantage that they only have limited solubility in organic solvents. Since these salts are used in amounts proportional to the adducts needed for the urea urethane synthesis, it is impossible to obtain highly concentrated product solutions without some unwelcome partial precipitation of the salts. Yet more highly concentrated solutions of urea urethanes are advantageous for manufacturing and storage reasons. If moreover lithium chloride is used, then the coating of corrosion-sensitive substrates using lithium chloride-containing thixotropic agents in the coating materials will frequently result in damage to the substrate.

The problem addressed by the present invention in view of European patent specification EP-B-1188779 was therefore that of retaining the advantages achieved therein of providing thixotropic agents which have a defined structure, possess a good storage stability of the solution over several months, are notable for broad compatibility in binders and hence provide more consistent use and of avoiding the disadvantages of using lithium salts and also N-methylpyrrolidone or comparably harmful solvents in their production and storage.

It was found that these problems are solved, surprisingly, when, in the process disclosed in European patent specification EP-B-1188779, not only the aprotic solvents specified therein but also the lithium salts used are replaced by ionic liquids.

Ionic liquids have a relatively high molecular weight and also an ionogenic character and hence are generally substantially or completely involatile and therefore can be regarded as free of volatile organic compounds. Since there are very many possible ways of combining cations and anions in ionic liquids, suitably choosing the cation and anion forming the ionic liquid makes it possible to adapt the compatibility and hence storage stability for different binder systems to distinctly superior effect than is possible with the solvent system of NMP and metal salt, since metal salts have only very limited solubility in organic solvents. It is a further surprising advantage that ionic liquids permit a distinct increase in the active content of the thixotropic agents combined with very good storage stability.

The present invention accordingly provides a method which comprises reacting at least two structurally different monohydroxy compounds of the general structure R—OH, where R is an n-alkyl radical or an iso-alkyl radical of 4 to 22 carbon atoms, an alkenyl radical of 3 to 18 carbon atoms, a cycloalkyl radical of 3 to 8 carbon atoms, an aralkyl radical of 5 to 12 carbon atoms, or a radical of the formula $C_mH_{2m+1}(O-C_nH_{2n})_x-$, $C_mH_{2m+1}(OOC-C_vH_{2v})_x-$ or $Z-C_6H_4(O-C_nH_{2n})_x-$ where m=1-22, n=2-4, x=1-15 and v=4 or 5 and Z is an alkyl radical of 1 to 12 carbon atoms, with a 1.5 to 5-fold excess of tolylene diisocyanate, to form monoisocyanate adducts, removing the unconverted tolylene diisocyanate from the reaction mixture and reacting the monoisocyanate adducts thus obtained with diamines of the formula $H_2N-R'-NH_2$, where R' corresponds to a radical $C_oH_{2o}$ where $o=2$ to 12, $(C_pH_{2p}\text{—}O)_q\text{—}C_pH_{2p}$ where $p=2$ to 4 and $q=1$ to 25,

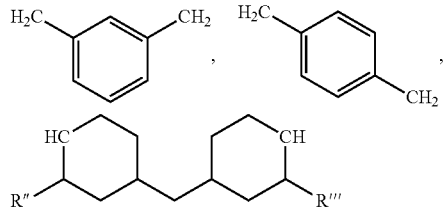

(R'' and R''' are each independently $CH_3$ or H), or

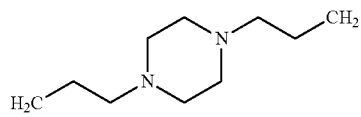

or mixtures thereof, in an ionic liquid to form urea adducts which carry two different radicals R.

The method does not require the use of solvent-stabilizing lithium compounds and so these are preferably not present in the thixotropic agent, i.e., the solution comprising urea urethanes. Furthermore, the reaction of the monoisocyanate adducts with diamines apart from the ionic liquids preferably does not utilize any further solvents, particularly not any solvents not generally recognized as safe by toxicologists. If further solvents other than the ionic liquids are used, particularly solvents generally recognized as safe by toxicologists, they preferably account for less than 20% by weight based on the overall weight of all solvents. When such solvents are used, they are preferably aprotic. Furthermore, the thixotropic agents obtainable by the method of the present invention preferably do not contain any halides, particularly no chlorides.

The solution comprising urea urethanes which is efficacious as a thixotropic agent is in principle obtainable by the method of the present invention in two different ways:

a) on the one hand, initially at least two structurally different alcohols R—OH are mixed and subsequently reacted with a 1.5 to 5-fold excess of tolylene diisocyanate. The unconverted tolylene diisocyanate is removed under gentle conditions, in accordance with the prior art, from the reaction mixture, and the mixture of structurally different monoisocyanate adducts which is obtained in this way is subsequently reacted with the diamines in an ionic liquid to form urea urethanes.

b) on the other hand, initially at least two structurally different alcohols R—OH are separately reacted with a 1.5 to 5-fold excess of tolylene diisocyanate. The unconverted tolylene diisocyanate is removed under gentle conditions, in accordance with the prior art, from the particular reaction mixture, and the structurally different monoisocyanate adducts obtained in this way are mixed with each other. The resulting mixture of structurally different monoisocyanate adducts is subsequently reacted with the diamines in an ionic liquid to form urea urethanes of the general structure (II).

The molar fraction of monoisocyanate adducts in the mixture of structurally different monoisocyanate adducts is between 20 and 80%, preferably between 35 and 65% and more preferably between 45 and 55%, wherein the sum total of the molar fractions of the monoisocyanate adducts is 100%.

The molar excess of tolylene diisocyanate is preferably in the range from 1.5 to 5.0 mol and more preferably in the range from 2.0 to 4.0 mol.

The solids content of the urea urethane solutions thus obtained is in the range from 5% to 80% by weight, preferably in the range from 20% to 60% by weight and more preferably in the range from 25% to 50% by weight, based on the overall weight of the urea urethane solution obtained. "Solids content" herein is to be understood as meaning the calculated urea urethane content resulting from the sum total of the weight percentages of the amine and of the isocyanate monoadduct.

The R—OH alcohols used for producing the monoisocyanate adducts are preferably linear or branched primary alcohols, which can be saturated or unsaturated, e.g., n-butanol, 2-ethylhexanol, isotridecyl alcohol, Guerbet alcohols of chain length $C_{10}$ to $C_{20}$, oleyl alcohol, linoleyl alcohol, lauryl alcohol, stearyl alcohol, but cycloaliphatic alcohols such as, for example, cyclohexanol or its alkyl-substituted derivatives, and also aromatically substituted alkanols such as benzyl alcohol are also suitable.

Particularly the alkoxylated derivatives of the above-recited alcohols are suitable for adjusting the polarity, whereby in this case lower alcohols of 1 to 6 carbon atoms such as methanol or allyl alcohol, for example, are also useful as starter component for alkoxylation. The products thus obtained preferably include ethylene oxide and/or propylene oxide and/or butylene oxide and/or styrene oxide units in the chain, and may include these units in alternating fashion or in blocks. Ethylene oxide and/or propylene oxide units are particularly preferred. Useful starter components for the alkoxylation further include aromatic alcohols such as phenols or alkylphenols for example.

To make the urea urethanes of the present invention compatible with state of the art binders, ester or polyester groups can be introduced into the alcohol component, for example by addition of lactones, such as ε-caprolactone for example, onto the above-recited alcohols or alcohol alkoxylates, or by using hydroxyl-functional (meth)acrylates.

The diisocyanates used to form the monoisocyanate adducts are essentially tolylene diisocyanates in the known and customary isomeric distribution, although the distillation of the excess portions of diisocyanate will result in shifts in the isomer content, which may result in the formation of higher proportions of 2,6-tolylene diisocyanate than is customarily on offer commercially. These distillates can be reused in the production of further monoadducts. Preference is given to tolylene diisocyanate isomers of 50 to 100 mol % 2,4-isomer content.

The diamines of the formula $H_2N\text{—}R'\text{—}NH_2$ are essentially linear diamines having a carbon chain length of 2 to 12 carbon atoms and being straight chain or branched, e.g., 1,3-propanediamine, hexamethylenediamine, octamethylenediamine, diaminododecane or neopentanediamine. Cyclic diamines such as 4,4'-diaminodicyclohexylmethane or 3,3'-dimethyl-4,4'-diaminodicyclohexylmethane for example are likewise suitable. Aromatic-aliphatic diamines such as meta- or para-xylylenediamine for example are particularly preferred. The diamines can also be used in urea formation as a mixture, since this reduces the tendency of the urea urethane to crystallize in solution.

The urea urethanes obtained by the process of the present invention contain neither free isocyanate groups nor free amino groups. "Free of isocyanate and amino groups" here is to be understood as meaning that the residual level of isocyanate groups is less than 0.01% based on the amount of monoadduct used, and the level of primary amino groups is less than 0.05% based on the amount of diamine used. The level of NCO and $NH_2$ groups can be determined titrimetrically. They are accordingly generally recognized as safe by physiologists. Nor are there any adverse secondary reactions with binders or fillers. The storage stability of these urea urethane solutions thus obtained is extremely high, amounting to as much as 12 months or more at standard storage temperature. The urea urethane solutions are also widely compatible in binders and thereby ensure a consistent use of the thixotropic agents.

The reaction of the monoisocyanate adduct mixtures with the diamine is carried out in an ionic liquid. The term "ionic liquids" herein is to be understood as meaning organic salts or mixtures of organic salts having melting points below 80° C., preferably below 50° C., more preferably below 30° C. and even more preferably below 20° C. The ionic liquids particularly preferred herein are liquid at room temperature (25° C.).

Several publications already describe the use of ionic liquids as solvents for transition metal-catalyzed reactions (review article: T. Welton, *Chem. Rev.* 1999, 99, 2071). Hydrogenations of olefins with rhodium(I) (P. A. Z. Suarez, J. E. L. Dullius, S. Einloft, R. F. de Souza and J. Dupont, *Polyhedron* 15/7, 1996, 1217-1219), ruthenium(II) and cobalt(II) complexes (P. A. Z. Suarez, J. E. L. Dullius, S. Einloft, R. F. de Souza and J. Dupont, *Inorganica Chimica Acta* 255, 1997, 207-209) were successful in ionic liquids having a tetrafluoroborate anion for example. The hydroformylation of functionalized and nonfunctionalized olefins is accomplished with rhodium catalysts in ionic liquids having weakly coordinating anions (e.g. $PF_6^-$, $BF_4^-$), EP-A-0776880, Y. Chauvin, L. Mussmann, H. Olivier, *Angew. Chem., Int. Ed. Engl.*, 1995, 34, 2698; W. Keim, D. Vogt, H. Waffenschmidt, P. Wasserscheid, *J. of Cat.*, 1999, 186, 481).

Binary ionic liquids of the $[A]^+[Y]^-$ type can be synthesized using a two-stage process (J. S. Wilkes, M. J. Zaworotko, *J. Chem. Soc., Chem. Commun.*, 13, 1992, 965) for example. The first stage comprises reacting an alkylating reagent $R^x$ and an amine $NR^1R^2R^3$ or a phosphane $PR^1R^2R^3$ in a quaternizing reaction to form the organic ammonium salt $[NR^1R^2R^3R]^+X^-$ or the organic phosphonium salt $[PR^1R^2R^3R]^+X^-$. $X^-$ is generally a halide ion. The organic halide salt is isolated and reacted in a subsequent, second reaction stage with the alkali or alkaline earth metal salt of the type $M^+[Y]^-$ in an exchange reaction. This takes place in a solvent in which the by-produced $M^+X^-$ is poorly soluble while the ionic liquid $[A]^+[Y]^-$ to be synthesized is readily soluble. To obtain ionic liquids having a halide anion, the synthesis can be discontinued after the first stage.

The two-stage process was successfully used in the literature to prepare ionic liquids having $[BF_4]^-$, $[PF_6]^-$, acetate, nitrate, $HSO_4^-$ or $SO_4^{2-}$ ions (J. S. Wilkes, M. J. Zaorotko, *J. Chem. Soc., Chem. Commun.*, 13, 1992, 965, B. Ellis, WO 9618459 A1 960620, 1996, J. Fuller, R. T. Carlin, H. C. de Long, D. Haworth, *J. Chem. Soc., Chem. Commun.*, 3, 1994, 299) for example.

Of disadvantage with this form of reaction is that quantitative exchange of the halide salt $[NR^1R^2R^3R]^+X^-$ or $[PR^1R^2R^3R]^+X^-$ to form the desired ionic liquid $[NR^1R^2R^3R]^+[Y]^-$ or, respectively, $[PR^1R^2R^3R]^+[Y]^-$ is only possible when the reaction system is completely anhydrous under exchange conditions. This is important particularly when ideally halide-free ionic liquids are to be obtained.

Since halide ions are disadvantageous for numerous applications of the thixotropic agents of the present invention in that they act as corrosion promoters in some applications and as a catalyst poison in others, it is advantageous to produce the thixotropic agents of the present invention using particularly such ionic liquids as contain no halide anion. "Halide-free" is applied to ionic liquids which do not contain significant amounts of halide ions as anion, the level of halide ions preferably being less than 0.1% by weight, more preferably less than 0.05% by weight and most preferably less than 0.01% by weight based on the total weight of the ionic liquid.

EP-A-1 182 197 discloses a one-stage process for producing such practically (almost) halide-free ionic liquids. The products obtainable by this process are also useful as a preferred reaction medium in the method of the present invention.

Particularly preferred ionic liquids usable in the method of the present invention have the general formula (I)

$$[A]_n^+[Y]^{n-},$$

where n is =1 or 2 and
the anion $[Y]^{n-}$ is selected from the group consisting of tetrafluoroborate $[BE]^-$, tetrachloroborate $[BCl_4]^-$, phosphate $[PO_4]^-$, alkylphosphate $[ROPO_3]^{2-}/[ROR'OPO_2]^-$, hexafluorophosphate $[PF_6]^-$, hexafluoroantimonate $[SbF_6]^-$, hexafluoroarsenate $[AsF_6]^-$, tetrachloroaluminate $[AlCl_4]^-$, trichlorozincate $[ZnCl_3]^-$, dichlorocuprate $[CuCl_2]^-$, sulfate $[SO_4]^{2-}$, alkylsulfate $[R'—SO_4]^-$, carbonate $[CO_3]^{2-}$, fluorosulfonate, $[R'—COO]^-$, $[R'—SO_3]^-$ or $[(R'—SO_2)_2N]^-$, and R, and R' is each independently a linear or branched aliphatic or alicyclic alkyl radical containing 1 to 12 carbon atoms, or a $C_5$-$C_{18}$-aryl, $C_5$-$C_{18}$-aryl-$C_1$-$C_6$-alkyl or $C_1$-$C_6$-alkyl-$C_5$-$C_{18}$-aryl radical, the hydrogen atoms of which can be wholly or partly replaced by halogen atoms. As mentioned, the anion $[Y]^{n-}$ can also be a halide such as $[F]^-$, $[Cl]^-$, $[Br]^-$ or $[I]^-$, although this would mean that the above-described disadvantages (corrosion) can be associated therewith depending on the intended use of the thixotropic agents.

The cation $[A]^+$ is preferably selected from quaternary ammonium cations, phosphonium cations or cations of N-containing heterocycles. Particularly preferred cations can be represented by the following structures:

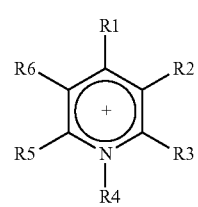

1

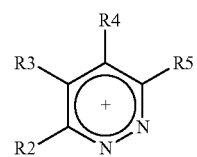

2

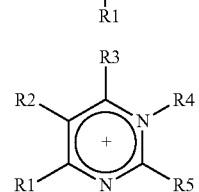

3

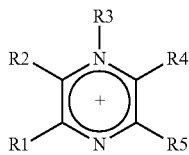
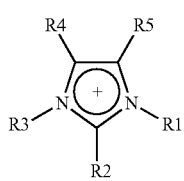
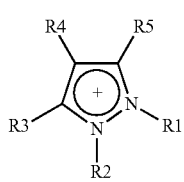
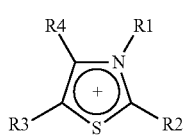
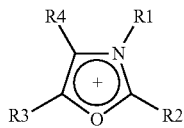
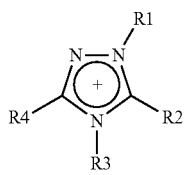
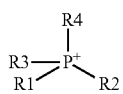
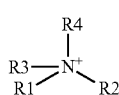
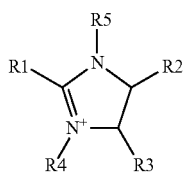
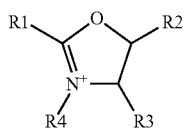

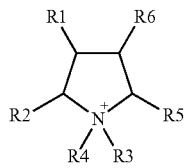
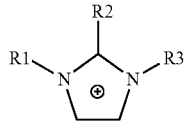

where the radicals R1, R2, R3, R4, R5 and R6 are each independently selected from the group consisting of (i) linear or branched, saturated or unsaturated, aliphatic or alicyclic alkyl groups of 1 to 20 carbon atoms, which can be substituted, for example with an alkyl group of 1-8 carbon atoms and/or halogen group, or unsubstituted; (ii) heteroaryl, heteroaryl-$C_1$-$C_6$-alkyl groups having 3 to 8 carbon atoms in the heteroaryl radical and at least one heteroatom selected from N, O and S, which radical can be substituted with at least one group selected from $C_1$-$C_6$-alkyl groups and/or halogen atoms; (iii) aryl, aryl-$C_1$-$C_6$-alkyl groups having 5 to 12 carbon atoms in the aryl radical, which may optionally be substituted with at least one $C_1$-$C_6$-alkyl group and/or a halogen atom; (iv) a linear or branched aliphatic and/or cycloaliphatic and/or aromatic hydrocarbon radical of 2-40 carbon atoms which is interrupted by one or more heteroatoms (N, O) and which can be substituted, for example with an alkyl group having 1-8 carbon atoms and/or halogen group, or unsubstituted; (v) a linear or branched aliphatic hydrocarbon radical of 2-20 carbon atoms which is interrupted by one or more functionalities selected from the group —O—C(O)—, —(O)C—O—, —NH—C(O)—, —(O)C—NH—, —(CH$_3$)N—C(O)—, —(O)C—N(CH$_3$)—, —S(O)$_2$—O—, —O—S(O)$_2$—, —S(O)$_2$—NH—, —NH—S(O)$_2$—, —S(O)$_2$—N(CH$_3$)—, —N(CH$_3$)—S(O)$_2$— and which can be substituted, for example with an alkyl group of 1-8 carbon atoms and/or halogen group, or unsubstituted. When hydrogen atoms on the abovementioned radicals R1, R2, R3, R4, R5 or R6 are substituted, the substituents do not bear any isocyanate-reactive groups such as hydroxyl or amino groups for example.

In a particular embodiment of the invention, the hydrogen atoms on alkyl, aryl, arylalkyl and alkylaryl sulfonate groups can be replaced by halogen atoms, more particularly fluorine, chlorine or bromine. Particular preference is given to the fluorinated, especially perfluorinated, alkyl and abovementioned aryl sulfonates, such as trifluoromethanesulfonate (triflate). Nonhalogenated representatives are the methanesulfonate, benzenesulfonate and toluenesulfonate groups, and also all further sulfonate leaving groups known in the prior art.

In a further embodiment of the invention, the hydrogen atoms on alkyl, aryl, arylalkyl and alkylaryl carboxylate groups can be replaced by halogen atoms, more particularly fluorine, chlorine or bromine. Particular preference is given to the fluorinated, especially perfluorinated, alkyl and abovementioned aryl carboxylates, such as trifluoromethanecarboxylate (trifluoroacetate; $CF_3COO^-$). Nonhalogenated representatives are the acetate and benzoate groups and also all further carboxylate leaving groups known in the prior art.

The halide anion $X^-$ in the alkylating agent RX is typically selected from the group consisting of chloride, bromide and iodide. The term "alkylating" comprehends arylalkylating and heteroarylalkylating with the stated groups as well as alkylating itself.

The cations of the ionic liquids used are preferably based on ammonium, pyridinium, pyrrolidinium, pyrrolium, oxazolium, oxazolinium, imidazolium, thiazolium or phosphonium ions and also mixtures thereof. The cations shall behave chemically inert to isocyanate groups.

Particular preference is given to cations based on imidazolium and oxazolium ions.

The anions are preferably selected from alkylsulfates, arylsulfates, sulfate, hydrogensulfate, phosphate, alkylphosphates, arylphosphates, tosylates, alkylborates, haloborates such as tetrafluoroborate for example, haloaluminates such as tetrachloroaluminate for example, carboxylates such as acetate and trifluoroacetate for example, perchlorate and also mixtures thereof.

Alkylsulfates, tosylates and acetates are particularly preferred.

The present invention further provides for the use of the urea urethane solution obtained by the process of the present invention for thixotroping coating materials. Coating materials are preferably aqueous, solvent-containing and solvent-free coatings, PVC plastisols, epoxy-based coatings and coatings based on unsaturated polyester resins.

The invention further provides solutions of the above-defined asymmetric urea urethanes in ionic liquids.

Exemplary embodiments will now be described to illustrate the essential features of the method of the present invention.

EXAMPLES

Table 1 lists the hereinbelow utilized monoadducts formed from TDI and a monoalcohol. Their preparation is described at length in the EP-B-1 188 779 patent specification. Examples 1 to 3 of the present invention correspond to examples 1 to 3 of EP 1 188 779 B1 and examples 4 to 6 of the present invention correspond to examples 5 to 7 of EP 1 188 779 B1.

TABLE 1 utilized monoadducts 1 (as per EP-B-1 188 779):

| Example | Alcohol | NCO content | Equivalent weight | TDI:alcohol molar ratio |
|---|---|---|---|---|
| 1 | butanol | 16.9% | 248 | 2.5:1 |
| 2 | butyl triglycol | 10.9% | 392 | 2.5:1 |
| 3 | isotridecanol | 11.3% | 372 | 3:1 |
| 4 | MPEG 350 | 8.0% | 525 | 3:1 |
| 5 | MPEG 500 | 6.2% | 675 | 3:1 |
| 6 | MPEG350/MPEG500 (molar ratio 1:1) | 7.0% | 600 | 2:1 |

TABLE 2 mixtures of monoadducts from table 1

| Mixture | Monoadduct mixture | Molar ratio |
|---|---|---|
| A | butyl triglycol/isotridecanol (from examples 2 + 3) | 1:1 |
| B | butyl triglycol/MPEG 500 (from examples 2 + 5) | 1:1.75 |
| C | butyl triglycol/MPEG 350/MPEG 500 (from examples 2 + 6) | 1:1:1 |

Comparative Example

As Per Example 8 of EP-B-1 188 779

At 80° C., 15.9 g of LiCl and 68 g of m-xylylenediamine are dissolved in 403 g of N-methylpyrrolidone. Then, 320 g of mixture A are metered in during 1 hour. On completion of the addition the mixture is stirred for a further 30 minutes and then cooled down to room temperature. The urea urethane solution thus obtained has a solids content of 50%.

Example 1

Inventive

A mixture of 68 g of m-xylylenediamine and 690 g of 1-ethyl-3-methylimidazolium ethylsulfate is prepared and heated to 60° C. Thereafter 472 g of mixture A are metered in during 1 hour. On completion of the addition the mixture is stirred for a further 30 minutes and then cooled down to room temperature. The urea urethane solution thus obtained has a solids content of 50%. A clear, homogeneous and liquid product is obtained.

Example 2

Inventive

A mixture of 68 g of m-xylylenediamine and 238 g of 1-ethyl-3-methylimidazolium ethylsulfate is prepared and heated to 60° C. Thereafter 472 g of mixture A are metered in during 1 hour. On completion of the addition the mixture is stirred for a further 30 minutes and then cooled down to room temperature. The urea urethane solution thus obtained has a solids content of 70%. A clear, homogeneous and liquid product is obtained.

Storage Stability

The appearance of the sample as a function of time is assessed by visual inspection. The results are summarized in table 3.

TABLE 3

| Sample | Appearance directly after preparation | Appearance after 1 year | Urea urethane content |
|---|---|---|---|
| comparative example | very cloudy, inhomogeneous, formation of sediment | inhomogeneous, sediment | 48% |
| Example 1 | clear, liquid, homogeneous | clear, liquid, homogeneous | 50% |
| Example 2 | clear, liquid, homogeneous | clear, liquid, homogeneous | 70% |

Determination of Level of Volatile Organic Compounds (VOC Content)

5 mg of a sample of the urea urethane solutions prepared under example are filled into a 20 ml head space vial and sealed air-tight. This vial, a glass tube 7 cm tall and 2 cm in diameter, is equilibrated at 100° C. for 1 hour and then analyzed by gas chromatography. Any peak eluting with a retention time between $C_6$ and $C_{16}$ is included in the evaluation.

The following result is obtained:

TABLE 4

| Sample | VOC content |
| --- | --- |
| comparative example | 156 000 ppm |
| Example 1 | <150 ppm |
| Example 2 | <150 ppm |

The determination is carried out using a 7694 headspace sampler from Agilent.

Performance Testing Results

To examine the anti-settling effect of the urea urethane solutions of the invention, pigment slurries were prepared and the sedimentation behavior was examined after 3 weeks' storage.

To prepare the pigment slurries, first a mixture of water, butyl glycol and Disperbyk 192 is prepared. This mixture is then added under agitation to the pigment, Iriodin 9303 Royal Gold WR II from Merck. Thereafter, the urea urethane solutions of the invention are incorporated, again under agitation using the Dispermat, for 2 minutes at a shear rate of 2 m/s.

To assess the sedimentation behavior, the slurries are introduced into a glass vessel (10 cm high, 1.5 cm in diameter) to a fill height of 7.5 cm. The syneresis is determined after 3 weeks' storage at room temperature.

Table 5 indicates the relative fractions of the individual components in the mixture.

TABLE 5

| | Control | Comparative example | Example 1 |
| --- | --- | --- | --- |
| Iriodin 9303 Royal Gold WR II | 30.0 | 30.0 | 30.0 |
| water | 64.5 | 64.5 | 64.5 |
| butyl glycol | 4.0 | 4.0 | 4.0 |
| Disperbyk 192 | 1.5 | 1.5 | 1.5 |
| urea urethane solution | — | 1.0 | 1.0 |

TABLE 6

| anti-settling effect | | | |
| --- | --- | --- | --- |
| | Control | Comparative example | Example 1 |
| total height | 7.5 cm | 7.5 cm | 7.5 cm |
| syneresis | 4.2 cm | 0.2 cm | 0 cm |

Corrosive Effect

To assess the corrosive effect of the additives used, the coatings recited in table 5 were filled into tinplate cans and sealed. The can was opened after 6 months and the appearance of the inside wall of the can was assessed by visual inspection. The results are listed in table 7.

TABLE 7

| corrosive effect | | |
| --- | --- | --- |
| | Comparative example | Example 1 |
| Appearance of can wall after 6 months | Can has rusted in many places severely in some instances | Unchanged |

The invention claimed is:

1. A method for producing a solution comprising urea urethanes, wherein the method comprises:

reacting monohydroxy compounds of the general structure R—OH, wherein R is selected from the group consisting of an n-alkyl radical or an iso-alkyl radical of 4 to 22 carbon atoms, an alkenyl radical of 3 to 18 carbon atoms, a cycloalkyl radical, an aralkyl radical, a radical of the formula $C_mH_{2m+1}(O\text{—}C_nH_{2n})_x\text{—}$, a radical of the formula $C_mH_{2m+1}(OOC\text{—}C_vH_{2v})_x\text{—}$, and a radical of the formula $Z\text{—}C_6H_4(O\text{—}C_nH_{2n})_x\text{—}$, wherein m=1-22, n=2-4, x=1-15, v=4 or 5, and Z is an alkyl radical of 1 to 12 carbon atoms, with a 1.5 to 5-fold excess of tolylene diisocyanate, removing the unconverted tolylene diisocyanate from the reaction mixture, and reacting the monoisocyanate adducts thus obtained with diamines of the formula $H_2N\text{—}R'\text{—}NH_2$, wherein R' is $C_oH_{2o}$ wherein $o$=2 to 12, $(C_pH_{2p}\text{—}O)_q\text{—}C_pH_{2p}$ wherein $p$=2 to 4 and $q$=1 to 25,

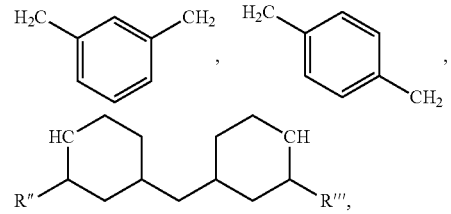

(wherein R" and R'" are each independently $CH_3$ or H),

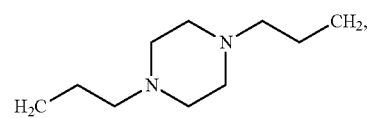

or mixtures thereof, to form urea urethanes, wherein the urea urethanes are produced by reacting at least two structurally different monoisocyanate adducts, which differ in the R radical, with the diamines, and wherein the reaction of the at least two structurally different monoisocyanate adducts with the diamines takes place in an ionic liquid;

wherein:

the ionic liquids have the general formula (I)

$[A]_n^+[Y]^{n-}$, wherein n is =1 or 2 and the anion $[Y]^{n-}$ is selected from the group consisting of tetrafluoroborate $[BF_4]^-$, tetrachloroborate $[BCl_4]^-$, phosphate $[PO_4]^{3-}$, alkylphosphate $[ROPO_3]^{2-}/[ROR'OPO_2]^-$, hexafluorophosphate $[PF_6]^-$, hexafluoroantimonate $[SbF_6]^-$, hexafluoroarsenate $[AsF_6]^-$, tetrachloroaluminate $[AlCl_4]^-$, trichlorozincate $[ZnCl_3]^-$, dichlorocuprate $[CuCl_2]^-$, sulfate $[SO_4]^{2-}$, alkylsulfate $[R'\text{—}SO_4]^-$, hydrogen sulfate, carbonate $[CO_3]^{2-}$, fluorosulfonate, $[R'\text{—}COO]^-$, $[R'\text{—}SO_3]^-$, and $[(R'\text{—}SO_2)_2N]^-$, wherein R and R' are each independently a linear or branched aliphatic or alicyclic alkyl radical containing 1 to 12 carbon atoms, or a $C_5$-$C_{18}$-aryl, $C_5$-$C_{18}$-aryl-$C_1$-$C_6$-alkyl or $C_1$-$C_6$-alkyl-$C_5$-$C_{18}$-aryl radical, the hydrogen atoms of which can be wholly or partly replaced by halogen atoms, and the cation [A]⁺ is selected from the group consisting of:

1
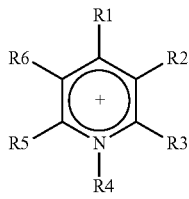

2
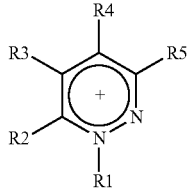

3
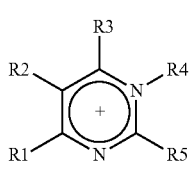

4
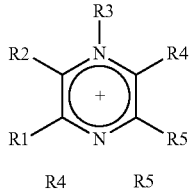

5
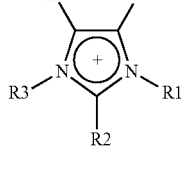

6
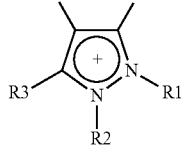

7
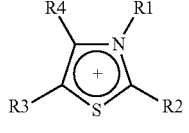

8
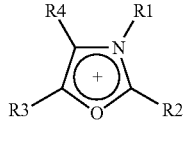

9
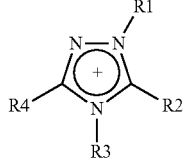

10
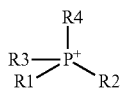

11
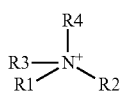

12
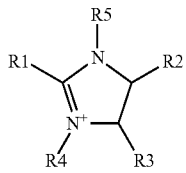

13
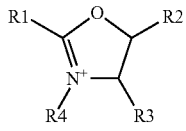

14
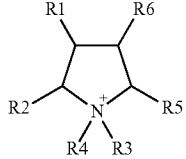

15
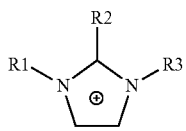

wherein the radicals R1, R2, R3, R4, R5 and R6 are each independently selected from the group consisting of (i) substituted or unsubstituted linear or branched, saturated or unsaturated, aliphatic or alicyclic alkyl groups of 1 to 20 carbon atoms; (ii) heteroaryl or heteroaryl-$C_1$-$C_6$-alkyl groups having 3 to 8 carbon atoms in the heteroaryl radical and at least one heteroatom selected from the group consisting of N, O, and S, wherein the radical can be substituted with at least one group selected from the group consisting of $C_1$-$C_6$-alkyl groups and halogen atoms; (iii) substituted or unsubstituted aryl or aryl-C1-C6-alkyl groups having 5 to 12 carbon atoms in the aryl radical; (iv) a group selected from the group consisting of linear or branched aliphatic, cycloaliphatic, and a substituted or unsubstituted aromatic hydrocarbon radical of 2-40 carbon atoms which is interrupted by one or more heteroatoms selected from the group consisting of N and O; and (v) a substituted or unsubstituted linear or branched aliphatic hydrocarbon radical of 2-20 carbon atoms which is interrupted by one or more functionalities selected from the group consisting of —O—C(O)—, —(O)C—O—, —NH—C(O)—, —(O)C—NH—, —(CH₃)N—C(O)—, —(O)C—N(CH₃)—, —S(O)₂—O—, —O—S(O)₂—, —S(O)₂—NH—, —NH—S(O)₂—, —S(O)₂—N(CH₃)—, and —N(CH₃)—S(O)₂—.

2. The method according to claim 1, wherein initially at least two structurally different alcohols R—OH are mixed and subsequently reacted with a 1.5 to 5-fold excess of tolylene diisocyanate, the unconverted tolylene diisocyanate is removed from the reaction mixture, and the mixture of structurally different monoisocyanate adducts which is obtained in this way is reacted with the diamines in an ionic liquid to form urea urethanes.

3. The method according to claim 1, wherein initially at least two structurally different alcohols R—OH are separately reacted with a 1.5 to 5-fold excess of tolylene diisocyanate, and the unconverted tolylene diisocyanate is removed from the reaction mixtures, and the structurally different monoisocyanate adducts obtained in this way are mixed with each other and the resulting mixture of structurally different monoisocyanate adducts is reacted with the diamines in an ionic liquid to form urea urethanes.

4. The method according to claim 2, wherein the molar fraction of the structurally different monoisocyanate adducts in the mixture is between 20 and 80%, wherein the sum total of the molar fractions of the monoisocyanate adducts is 100%.

5. The method according to claim 1, wherein a solution having a solids content of 5% to 80% by weight is produced.

6. The method according to claim 1, wherein the molar excess of tolylene diisocyanate is in the range from 2 to 4.

7. The method according to claim 1, wherein a tolylene diisocyanate isomer mixture having a 2,4-isomer fraction in the range from 50% to 100% by weight is used.

8. The method according to claim 1, wherein the ionic liquid is liquid at 25° C.

9. A thixotropic coating solution prepared according to the method of claim 1.

10. A solution in an ionic liquid of the urea urethane defined according to claim 1.

11. The method according to claim 1, wherein the ionic liquids have the general formula (I)

wherein n is=1 or 2 and
the cation $[A]_n^+$ is selected from the group consisting of

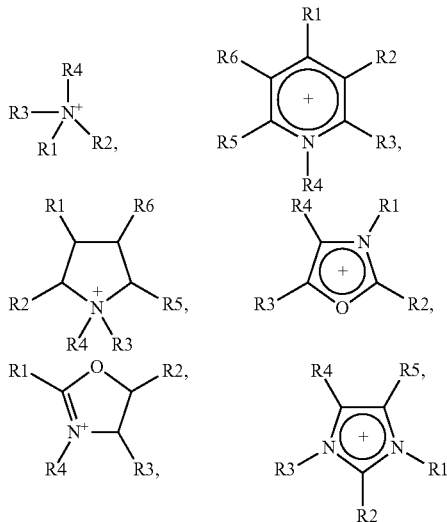

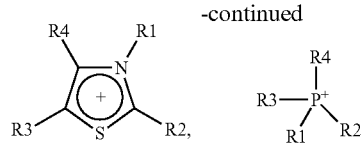

and mixtures thereof.

12. The method according to claim 11, wherein the cation $[A]_n^+$ is selected from the group consisting of

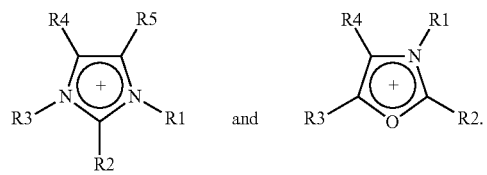

13. The method according to claim 1, wherein the ionic liquids have the general formula (I)

wherein n is=1 or 2 and
the anion $[Y]^{n-}$ is selected from the group consisting of $[R'—SO_4]^-$, $[SO_4]^{2-}$, hydrogen sulfate, phosphate $[PO_4]^{3-}$, alkylphosphate $[ROPO_3]^{2-}/[ROR'OPO_2]^-$, tosylates, tetrafluroborate $[BF_4]^-$, tetrachloroborate $[BCl_4]^-$, $[R'—COO]^-$, and mixtures thereof.

14. The method according to claim 13 wherein the anion $[Y]^{n-}$ is selected from the group consisting of alkyl sulfates, tosylates, and acetates.

15. The method of claim 1, wherein (i) the linear or branched, saturated or unsaturated, aliphatic or alicyclic alkyl groups of 1 to 20 carbon atoms are substituted with an alkyl group of 1-8 carbon atoms or a halogen atom.

16. The method of claim 1, wherein (iii) the aryl or the aryl-$C_1$-$C_6$-alkyl groups having 5 to 12 carbon atoms in the aryl radical is substituted with a $C_1$-$C_6$-alkyl group or a halogen atom.

17. The method of claim 1, wherein (iv) the aromatic hydrocarbon radical of 2-40 carbon atoms, which is interrupted by one or more heteroatoms selected from the group consisting of N and O, is substituted with at least one of an alkyl group having 1-8 carbon atoms and a halogen atom.

18. The method of claim 1, wherein (v) the substituted or unsubstituted linear or branched aliphatic hydrocarbon radical of 2-20 carbon atoms which is interrupted by one or more functionalities selected from the group consisting of —O—C(O)—, —(O)C—O—, —NH—C(O)—, —(O)C—NH—, —(CH$_3$)N—C(O)—, —(O)C—N(CH$_3$)—, —S(O)$_2$—O—, —O—S(O)$_2$—, —S(O)$_2$—NH—, —NH—S(O)$_2$—, —S(O)$_2$—N(CH$_3$)—, and —N(CH$_3$)—S(O)$_2$— is substituted with an alkyl group of 1-8 carbon atoms or a halogen atom.

* * * * *